United States Patent [19]

Kogut et al.

[11] Patent Number: 5,698,193
[45] Date of Patent: Dec. 16, 1997

[54] METHOD OF TREATING BIRDS

[75] Inventors: Michael H. Kogut; John R. DeLoach; Billy M. Hargis, all of College Station, Tex.; Edward D. McGruder, Fishers, Ind.

[73] Assignees: The United States of America as represented by the Department of Agriculture, Washington, D.C.; The Texas A&M University System, College Station, Tex.

[21] Appl. No.: 364,484

[22] Filed: Dec. 27, 1994

[51] Int. Cl.⁶ .......................... A01K 45/00; A61K 38/19
[52] U.S. Cl. .............................. 424/85.1; 119/6.8
[58] Field of Search ................ 530/351; 424/85.1, 424/85.2; 118/6.8, 348

[56] References Cited

U.S. PATENT DOCUMENTS

| | | | |
|---|---|---|---|
| 5,028,421 | 7/1991 | Fredericksen et al. | 424/85.2 |
| 5,034,513 | 7/1991 | Fredericksen et al. | 530/351 |
| 5,106,617 | 4/1992 | Fredericksen et al. | 424/85.2 |
| 5,474,769 | 12/1995 | Grabstein et al. | 424/85.2 |

OTHER PUBLICATIONS

Hu, Y. et al. Disturbed Immuno–Endocrine Communication. *International Archives of Allergy and Immunology.* 1993, vol. 102, pp. 232–241.

M.H. Kogut, et al.; Dynamics of the Avian Inflammatory Response to Salmonellia–immune lymphokines: changes in avian blood leukocyte populations. *Inflammation* 18: 373–388 (1984).

G.L. Tellez, et al.; Immunoprophylaxis of Salmonella enteritidis (SE) infection by lymphokines in Leghorn chicks. *Avian Dis.* 37:1062–1070 (1993).

E.D. McGruder, et al.; Salmonella enteritidis immune leukocyte-stimulated soluble factors: effects on increased resistance to Salmonella organ invasion in day–old Leghorn chicks. *Poultry Sci.* 72:2264–2271 (1993).

M.H. Kogut and T. Slajchert; T. lymphocytes induce protection in chickens against *Eimeria tenella* by production of lymphokines. *Immunol. Infect. Dis.* 2:69–80 (1992).

J.M. Sharma and B.R. Burmester; Resistance to Marek's disease at hatching in chickens vaccinated as embryos with the turkey herpesvirus. *Avian Dis.* 29:134–139 (1982).

M.H. Kogut, et al.; In Ovo Administration Of Salmonella Enteritidis (SE)–Immune Lymphokines Conferred Protection Against SE Organ Infectivity In Neonatal Chicks. *Poultry Science*, vol. 73, Suppl. 1 (1994), p. 44.

*Primary Examiner*—Jeffrey E. Russel
*Attorney, Agent, or Firm*—M. Howard Silverstein; Randall E. Deck; John D. Fado

[57] ABSTRACT

A method of combatting microbial infections, including *Escherichia coli* and *Salmonella* infections, in immature birds by in ovo administration of an immune lymphokine (ILK) containing preparation in an amount effective to combat microbial infections in immature birds. A method of combatting microbial infections in immature birds by upregulating the production of endogenous Interleukin-8 (IL-8) in the bird. A method of combatting microbial infections in immature birds by in ovo administration of immune lymphokine (ILK).

19 Claims, No Drawings

METHOD OF TREATING BIRDS

FIELD OF THE INVENTION

This invention relates to the treatment of birds in ovo by the administration of immune lymphokines to combat microbial infections.

BACKGROUND OF THE INVENTION

Hatching birds are exposed to pathogenic microbes, including bacteria, which are liberated from the broken shells and shell membranes. Bacteria which are inhaled or ingested can colonize respiratory or gastrointestinal mucosa and may penetrate the epithelial barriers. Hatchlings are initially protected against pathogens by maternally derived antibodies. However, maternal antibodies provide only temporary protection during the period before and after hatching when the bird's own immune system is immature. Often maternal antibody levels wane before natural antibody synthesis can adequately protect the immature bird against pathogens, causing reduced antibody levels. This period of reduced antibody levels occurs between weeks two and three posthatch and is often associated with bacterial pathogen-associated peaks in mortality, specifically colisepticemia, at three to four weeks posthatch.

The present invention arose from our investigations into the biological activity of avian IL-2 in vivo. A particularly important finding disclosed herein is that when a preparation of immune lymphokines obtained from pre-stimulated lymphocytes is administered to birds in ovo, resistance to microbial infections is increased in the hatched birds.

SUMMARY OF THE INVENTION

A method of treating a microbial infection in a bird is disclosed herein. The method comprises administering to a bird in ovo an immune lymphokine (ILK) preparation in an amount effective to combat microbial infections in the hatched bird.

Another aspect of the present invention is a method of treating a microbial infection in a bird, comprising upregulating the production of endogenous Interleukin-8 (IL-8) in the bird.

A further aspect of the present invention is a method of treating a microbial infection in a bird, comprising administering to the bird in ovo an immune lymphokine obtained from a donor avian which has been stimulated or immunized with an immunogen in an effective microbe-combatting amount.

Also disclosed herein is the use of the ILK preparation as described above for the preparation of a medicament for carrying out the methods of in ovo treatment as described herein.

DETAILED DESCRIPTION OF THE INVENTION

The terms "bird" and "avian" as used herein, are intended to include males or females of any avian species, but are primarily intended to encompass poultry which are commercially raised for eggs or meat. Accordingly, the terms "bird" and "avian" are particularly intended to encompass hens, cocks and drakes of chickens, turkeys, ducks, geese, quail and pheasant. Chickens and turkeys are preferred.

The term "in ovo," as used herein, refers to birds contained within an egg prior to hatch. Thus, the present invention may be conceived of as both a method of treating eggs and a method of treating birds. The present invention may be practiced with any type of bird egg, including chicken, turkey, duck, goose, quail, and pheasant eggs. Chicken and turkey eggs are preferred, with chicken eggs most preferred. Eggs treated by the method of the present invention are fertile eggs which are preferably in the fourth quarter of incubation. Chicken eggs are treated on about the fifteenth to nineteenth day of incubation, and are most preferably treated on about the eighteenth day of incubation (the eighteenth day of embryonic development). Turkey eggs are preferably treated on about the twenty-first to twenty-sixth day of incubation, and are most preferably treated on about the twenty-fifth day of incubation.

In general, an immune lymphokine (ILK) preparation may be made by: administering an immunogen (preferably a live immunogen) to a donor animal in an amount effective to stimulate, activate, or induce the T-cells of that animal; collecting the T-cells from that donor animal; and stimulating those T-cells in vitro with a T-cell mitogenic agent to produce a conditioned medium containing ILK. The conditioned medium may be used as an ILK preparation. Any animal may be used as the donor animal, including mammalian species (e.g. ovine, bovine, human, etc.) and avian species (e.g. chicken, turkey, duck). Avian species are preferred.

In brief, an avian ILK preparation may be obtained by administering an immunogen (preferably a live immunogen) to a donor avian in an amount effective to stimulate, activate, or induce the T-cells of that avian; collecting lymphocytes from that donor avian (most conveniently from the spleen of the donor avian); and growing the lymphocytes in a medium (preferably a serum-free medium) containing a T-cell mitogenic agent such as Concanavalin A to produce a conditioned medium containing ILK. The medium upon which lymphocytes have been grown (the "conditioned medium") may itself be used as an ILK preparation to administer the active agent. Optionally, the ILK active fractions may be recovered from the conditioned medium and used as the ILK preparation.

Immunogens used to stimulate the donor animal include, but are not limited to, viral, bacterial and protozoal immunogens. Where avian donors are used, suitable bacterial immunogens include, but are not limited to, Salmonella spp. such as *Salmonella enteritidis*, and protozoal immunogens include Eimeria spp. such as *Eimeria tenella*.

While the degree of purity of the ILK is not critical to practicing the present invention, it is preferably at least substantially serum free, and may optionally be mitogen-free. A crude ILK preparation may be purified by any of a variety of standard separation procedures as are known in the art.

The ILK preparations as described above may also be used for the preparation of a medicament for carrying out the methods of in ovo treatment as described herein.

An increased resistance to *Salmonella enteritidis* (SE) organ infectivity has been described in chickens following the prophylactic administration of SE-immune lymphokines (SE-ILK; ILK obtained from donor avians stimulated with *Salmonella enteritidis*). Tellez et al., *Avian Dis.* 37, 1062 (1993); McGruder et al., *Poultry Science*, 72, 2264 (1993). Resistance was associated with a significant increase in the number of circulating heterophils within 4 hours of SE-ILK injection. The most pronounced feature of the SE-ILK induced protection in chicks was the specific accumulation of heterophils at the site of bacterial invasion. Tellez et al., supra.

While not wishing to be bound to any particular theory of the instant invention, it appears that the ILK preparation contains an activity which upregulates endogenous Interleukin-8 production in the animal being treated. Interleukin-8 (IL-8) is a potent neutrophil chemotactic factor released by a variety of cell types in animals in response to infection and injury. See Streiter et al., *J. Lab. Clin. Med.* 123, 183 (1994). Accordingly, the present invention may be carried out by any means of upregulating the endogenous IL-8 production of the bird in ovo.

The term "Interleukin-8" (IL-8) as used herein, refers to the polypeptide which is produced by stimulated mammalian or avian peripheral blood lymphocytes, endothelial cells, and monocytes, and which has been identified previously by names such as neutrophil-activating peptide and neutrophil chemotactic factor. See generally M. Gimbrone, et al., *Science* 246:1601, 1603 n. 14 (1989). This compound is known, see Yoshimura, T., et al., *Proc. Natl. Acad. Sci. USA* 84:9233-9237 (1987). Interleukin-8 used in the present invention may be of any species of origin, including mammalian (e.g. ovine, bovine, human, etc.) and avian (e.g. chicken, turkey, duck, etc.). The IL-8 polypeptide is produced in various lengths depending upon the cell of origin thereof. In practicing the methods of the present invention, IL-8 originating from any cell type, including blood lymphocytes, endothelial cells, and monocytes, may be employed; IL-8 obtained from lymphocytes and/or monocytes is preferred. These compounds are known. See, e.g., M. Gimbrone et al. supra; M. Baggiolini and K. Clemetson, PCT Application WO 90/06321; H. Aschauer and P. Peveri, PCT Application WO 89/04836. Human endothelial cell IL-8 is commercially available from Genzyme, Inc., (Boston, Mass.).

The term IL-8 includes active fragments thereof. Active fragments of Interleukin-8 are peptides derived from Interleukin-8 which have N-terminal, C-terminal, or both N-terminal and C-terminal amino acid residues deleted, but which retain the biological activity of Interleukin-8 as described herein.

When practicing the present invention, the immune lymphokine administered may be related in origin to the species to which it is administered or be obtained from a different species. When treating avians, avian IL-8 may be used if desired.

In practicing the present invention, the active agent is administered in an effective microbe-combatting amount, which may be determined by one skilled in the art using known techniques. The amount administered will vary depending on the age, weight and condition of the subject being treated, but is generally a dose equivalent to from about 1 to about 1,000 μL of ILK preparation as described below.

As used herein, the term "treat" or "treating" a microbial infection refers to a prophylactic treatment which increases the resistance of a subject to infection with a pathogen or, in other words, decreases the likelihood that the subject will become infected with the pathogen. A method of treating Salmonella infection in an avian thus refers to a method which increases the treated avian's resistance to infection by Salmonella spp., as compared to an untreated avian. Treatment using the methods of the present invention results in an inhibition of, or combatting of, the growth of microbial pathogens.

As used herein, the term "upregulate" or "upregulating" refers to inducing an increase in production, secretion or availability (and thus an increase in the concentration) of a protein or peptide. A method of upregulating endogenous IL-8 in an avian thus refers to a method of inducing an increase in the production, secretion or availability of IL-8 in the avian, as compared to an untreated avian.

The present invention may be used to combat any type of microbial infection, including viral infections (e.g., mammalian viruses such as Japanese Encephalitis Virus, Influenza Virus, Sendai Virus, Measles Virus, Human Influenza Virus and Rabies, etc.; avian viruses such as Marek's disease, Rous Sarcoma Virus, Infectious Bursal Disease Virus, Newcastle's Disease, Infectious Bronchitis Virus, etc.), protozoal infections (e.g., coccidiosis infections such infections caused by *Eimeria tenella* and infections by other Eimeria species, such as *E. acervulina, E. mivati, E. mitis, E. praecox, E. hagani, E. necatrix, E. maxima*, and *E. brunetti*), fungal infections (e.g., Aspergillus infections), and bacterial infections.

The present invention may be used to combat all forms of virus, including retroviruses, RNA viruses and DNA viruses. Retroviruses that may be combatted include retroviruses of both animals and man. This group of retroviruses includes both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV). The foregoing list is illustrative, and is not intended to be limiting.

Examples of other RNA viruses that may be combatted by the present invention include, but are not limited to, the following: members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, murine rotavirus, simian rotavirus, bovine or ovine rotavirus, avian rotavirus); the family Picornaviridae, including the genus Enterovirus (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), the genus Rhinovirus (Human rhinoviruses including at least 113 subtypes; other rhinoviruses), the genus Apthovirus (Foot and Mouth disease (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); the family Rhabdoviridae, including the genus Vesiculovirus (VSV), Chandipura virus, Flanders-Hart Park virus), the genus Lyssavirus (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Mouse Hepatitis virus, Human enteric corona virus, and Feline infectious peritonitis (Feline coronavirus).

Illustrative DNA viruses that may be combatted by the present invention include, but are not limited to: the family Poxviridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheeppox, goatpox), the genus Suipoxvirus (Swinepox), the genus Parapoxvirus (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A,B,C,D,E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc). Finally, DNA viruses may include viruses which do not fit into the above families such as Kuru and Creutzfeldt-Jacob disease viruses and chronic infectious neuropathic agents (CHINA virus).

The present invention may be used to combat both gram negative and gram positive bacterial infections. Such gram positive bacteria include, but are not limited to, Pasteurella species, Staphylococci species, and Streptococcus species. Gram negative bacteria include, but are not limited to, *Escherichia coli*, Pseudomonas species, and Salmonella species. *Salmonella enteritidis* is an important pathogen in the commercial layer industry, as ovavian colonization of layers may result in maternally transmitted Salmonella in table eggs.

The term "colisepticemia" as used herein refers to septicemic *E. coli* infections caused by invasive *E. coli* bacteria. While some strains of *E. coli* are noninvasive, invasive strains exist that are able to invade host tissue and cause severe disease. The manner by which colisepticemia is transmitted among poultry is not yet well understood.

Eggs may be administered the active composition by any means which transports the composition through the shell. The preferred method of administration is, however, by injection. The site of injection is preferably within either the region defined by the amnion, including the amniotic fluid and the embryo itself, in the yolk sac, or in the air cell. By the beginning of the fourth quarter of incubation, the amnion is sufficiently enlarged that penetration thereof is assured nearly all of the time when the injection is made from the center of the large end of the egg along the longitudinal axis.

The mechanism of injection is not critical, but it is preferred that the method not unduly damage the tissues and organs of the embryo or the extraembryonic membranes surrounding it so that the treatment will not decrease hatch rate. A hypodermic syringe fitted with a needle of about 18 to 22 gauge is suitable for the purpose. To inject into the air cell, the needle need only be inserted into the egg about two millimeters. A one inch needle, when fully inserted from the center of the large end of the egg, will penetrate the shell, the outer and inner shell membranes enclosing the air cell, and the amnion. Depending on the precise stage of development and position of the embryo, a needle of this length will terminate either in the fluid above the chick or in the chick itself. A pilot hole may be punched or drilled through the shell prior to insertion of the needle to prevent damaging or dulling of the needle. If desired, the egg can be sealed with a substantially bacteria-impermeable sealing material such as wax or the like to prevent subsequent entry of undesirable bacteria.

It is envisioned that a high speed automated injection system for avian embryos will be particularly suitable for practicing the present invention. Numerous such devices are available, exemplary being those disclosed in U.S. Pat. Nos. 4,903,635 and 4,681,063 to Hebrank, U.S. Pat. No. 5,056, 464 to Lewis, U.S. Pat. Nos. 5,136,979 and 5,176,101 to Paul et al., and U.S. Pat. Nos. 4,040,388, 4,469,047, and 4,593,646 to Miller (the disclosures of all U.S. patent references cited herein are to be incorporated herein by reference). All such devices, as adapted for practicing the present invention, comprise an injector containing avian immune lymphokine as described herein, with the injector positioned to inject an egg carried by the apparatus with the avian IL-8. Other features of the apparatus are discussed above. In addition, if desired, a sealing apparatus operatively associated with the injection apparatus may be provided for sealing the hole in the egg after injection thereof.

Preferred apparatus for practicing the present invention are disclosed in U.S. Pat. Nos. 5,136,979 and 5,176,101 to Paul et al., U.S. Pat. No. 4,903,635 to Hebrank and U.S. Pat. No. 5,056,464 to Lewis, the disclosures of which are incorporated herein by reference. These devices comprise an injection apparatus for delivering fluid substances into a plurality of eggs and apparatus for aligning the eggs in relation to the injection apparatus. The features of these apparatus may be combined with the features of the apparatus described above for practicing the present invention. In practicing the present invention, injected eggs are incubated to hatch and the birds are raised to at least 2 weeks of age.

The following examples are provided to more fully illustrate the present invention, and are not to be taken as restrictive thereof. In the following examples, cfu means colony forming units; μg means micrograms; μL means microliters; μM means micromolar; mL means milliliters; cm means centimeters; nm means nanometers; ° C. means degrees Celsius; g means grams; g means gravity; kDa means kilodaltons; BGA means brilliant green agar; Con A means Concanavalin A; SE means *Salmonella enteritidis;* RPMI means Roswell Park Memorial Institute Medium; ILK means immune lymphokines; NILK means non-immune lymphokines; EDTA means disodium ethylenediaminetetraacetic acid; XTT means 3,3'-[1[(phenylamino) carbonyl]-3,4-tetrazolium]-bis(4-methoxy-6-nitro) benzene sulfonic acid hydrate; NO means novobiocin; NA means nalidixic acid; HBSS means Hanks Balanced Salt Solution.

EXAMPLE 1

Materials and Methods

In the following procedures, novobiocin, nalidixic acid, RPMI, methyl a-mannopyranoside, Concanavalin A, EDTA, 1% methylcellulose, HBSS, Ficoll-Hypaque gradient, Triton X-100, XTT, and 2,3-dimethoxy-5-methyl-1,4-benzoquinone were obtained from Sigma Chemical Co. (St. Louis, Mo.); brilliant green agar (BGA) was obtained from Difco Laboratories (Detroit, Mich.); Diff-Quik-stained cytospin was obtained from Shahdon Scientific (Pittsburgh, Pa.); YM-10 membranes were obtained from the Amicon Corp. (Beverly, Mass.).

1. Experimental Animals

Naive, day-of-hatch Single Comb White Leghorn chicks were obtained from a commercial hatchery and randomly placed in electrically heated starter battery cages located within a P2 biological hazard isolation unit. Upon arrival, 20 chicks were determined to be feces- and organ-culture negative for Salmonella. Chicks were provided ad libitum access to water and a balanced, unmedicated corn-soybean ration that met or exceeded the levels of critical nutrients recommended by the National Research Council. Before use, the feed was cultured for Salmonellae using standard culture methods (Andrews, et al., *Bacteriological Analytical Manual,* 5th Edition, pp. 1–29(1978)). *Salmonellae* serovars were not detected in the feed.

2. Preparation of Bacterial Isolates

A primary poultry isolate of *Salmonella enteritidis* (SE), SE phage type 13a, was obtained from the National Veterinary Sciences Laboratory. The isolate, which was resistant to novobiocin (NO) and nalidixic acid (NA) was lyophilized and stored in aliquots of $1 \times 10^9$ cfu at $-70°$ C. until used. Medium used to culture the resistant isolate in experimental studies contained 25 μg/mL NA to inhibit the growth of the other bacteria, and thereby serve as markers for the selected particular isolate of SE. To prepare the inocula for the SE challenge, 3 mL of phosphate-buffered saline was used to resuspend the lyophilized bacteria, and 150 μL of the suspension was incubated at 37° C. for 6 hours in 10 mL of tryptose soy broth. After incubation, 100 μL of that suspension was incubated at 37° C. for 6 hours in 10 mL of tryptose soy broth. After this incubation, 100 μL of the new suspension was incubated at 37° C. for 18 hours in 10 mL of tryptose soy broth. The concentration of SE was adjusted to $1 \times 10^9$ cfu/mL by diluting the suspension with phosphate-buffered saline according to a standard curve previously generated using a spectrophotometer (0.6 absorbance), with a reference wavelength of 625 nm (Model Spectronic 20D, Milton Roy Co., Rochester, N.Y.). For challenge, this reference concentration was diluted in phosphate-buffered saline to a calculated concentration of $1 \times 10^5$ cfu/mL. The viable bacterial cell concentration was verified by colony counts on brilliant green agar (BGA).

3. Preparation of Immune Lymphokines

The preparation of ILK has been previously published in detail (see McGruder et al., *Poultry Sci.* 72:2265–2271 (1993); Tellez et al., *Avian Dis.* 37:1062–1070 (1993); Kogut et al., *Inflammation* 18:373–388 (1994)). Immune lymphokine was prepared from culture supernatants of Concanavalin A-stimulated T-cells derived from adult hens hyperimmunized with SE. Briefly, 40-wk-old, Salmonella-free White Leghorn hens were challenged with SE by oral administration of $1 \times 10^8$ cfu SE given three times over a three-week period. After the third SE challenge, hens were euthanized and splenic T-cells were isolated from hens according to the procedure originally described by Julius et al. (see *Eur. J. Immunol.* 29:497–508 (1973)) and modified by Kogut and Slajchert (see *Immunol. Infect. Dis.* 2:69–80 (1992)). A monolayer of isolated T-cells, adjusted to a concentration of $1 \times 10^7$ viable cells per milliliter, was cultured in RPMI 1640 medium containing 7.5 μg/mL of Con A, for 48 hours at 37° C. in a 5% $CO_2$ incubator. After incubation, supernatant fluids were collected and residual Con A was inactivated with the inhibitor, methyl a-mannopyranoside. The supernatants were concentrated fivefold by ultrafiltration using YM-10 membranes (10 kDa cutoff), filtered through a 0.45 μM filter, and stored at $-20°$ C. until used. Non-immune ILK (NILK) was prepared in a similar manner from T-cells derived from Salmonella-free hens.

4. In ovo Administration of Immune Lymphokines

The in ovo administration of ILK followed the procedure originally described by Sharma and Burmester (see *Avian Dis.* 26:134–149 (1982)) and modified. Briefly, on day 18 of embryogenesis, fertile eggs were wiped at the large end with 70% ethanol, gently scored with an 18-gauge needle, and either (1) injected into the amnion at a depth of 3.5 cm at the large end of the egg with either ILK or NILK using a tuberculin syringe with a 25-gauge, 4 cm needle, or (2) were not injected (untreated). The injection site was sealed with melted paraffin, and the eggs were set in a commercial hatcher at 99° C. for the remaining incubation period. The same lot of ILK and NILK was used for all experiments.

5. Isolation of Peripheral Blood Heterophils

Avian heterophils were isolated from the peripheral blood of day-old White Leghorn chicks as described by Andreasen and Latimer (*Avian Dis.* 33:163–167 (1989)). EDTA anticoagulated blood was mixed with 1% methylcellulose at 1.5:1 ratio and centrifuged at 25×g for 5 minutes. The serum and buffy coat layers were retained and suspended in Hanks Balanced Salt Solution (HBSS, 1:1) without calcium and magnesium. This suspension was layered over a discontinuous Ficoll-Hypaque gradient (specific gravity 1.077 over specific gravity 1.119). The gradient was then centrifuged at 250×g for 25 minutes. After centrifugation, the 1.077–1.119 interface and 1.119 band containing heterophils was collected, washed twice in RPMI 1640 medium, and resuspended in fresh RPMI 1640 medium. Cell viability was routinely >95% as determined by trypan blue exclusion (Freshney, *Culture of Animal Cells Vol.* 1 (1983)). The purity of the heterophil suspension was assessed by microscopic examination of Diff-Quik-stained cytospin smears. Heterophil preparations obtained by this method were typically >95% pure. The cell concentration was adjusted to $2\times10^6$ heterophils per milliliter and stored on wet ice until used.

6. Statistical Analysis Methods

The chi-square test of independence was used to determine significant differences in hatchability, bactericidal activity and SE organ invasion between treatment groups (see Zar, J., *Biostatistical Analysis*, 2nd Ed., Prentice-Hall, Inc., pp. 384–351 (1984)). Significant differences in hatch weights between treatment groups were determined using the General Linear Models procedure of "SAS", and significance was further separated using Duncan's multiple range test (Luginbuke, R. C. and Schlotzhaver, S. D., "SAS/STAT" *Guide For Personal Computers* 6th Ed., pp. 555–573 (1987); *SAS Users Guide: Statistics* (1982)). Pooled data was reported at the P<0.05 level.

EXAMPLE 2

Effect of In Ovo Administration of ILK on Hatchability and Hatch Weight

On Day 18 of embryogenesis, 340 (Trial 1) and 234 (Trial 2) fertile White Leghorn eggs were randomly divided into three treatment groups. Treatment groups included the following: untreated, NILK and ILK. Injections were made either into the amnion of eggs with 100 µL of either NILK or ILK, or were not injected (untreated). At hatch, percentage hatchability was calculated and hatch weights were recorded. Hatchability and hatch weight data were collected over two separate trials.

Table 1 shows the effect of in ovo administration of ILK to fertile eggs on hatchability. In two trials, there was no difference in percentage hatchability for the in ovo injection of either ILK or NILK as compared with untreated chicks. Mean percentage hatchability in Trials 1 and 2 was approximately 80 and 92%, respectively. The target percentage hatchability for these commercial chicks was 86%.

Table 1 also shows the effect of in ovo administration of ILK to fertile eggs on hatch weights. In trials 1 and 2 there was a 1.0 and 0.8 g reduction, respectively, in hatch weights of chicks treated in ovo with ILK. This reduction was significant in Trial 1, but was not significant in Trial 2. It should be noted that in all trials hatch weights of ILK-treated chicks were greater than the minimum target hatch weight of 33 g for these commercial chicks.

TABLE 1

Effect of in ovo administration of immune or nonimmune lymphokines to 18-d chick embryos on percentage hatchability and hatch weights.

| Trial | In ovo treatment | Hatchability[1] | Hatch weights[2] (g) |
|---|---|---|---|
| 1 | control | 88/114 (77) | 39.9 ± 0.3[a] |
|   | NILK    | 89/113 (79) | 39.9 ± 0.3[a] |
|   | ILK     | 94/113 (83) | 38.9 ± 0.3[b] |
| 2 | control | 68/74 (92)  | 41.2 ± 0.3 |
|   | NILK    | 74/80 (92)  | 41.2 ± 0.3 |
|   | ILK     | 78/80 (97)  | 40.4 ± 0.3 |

[a,b]Values in a column with no common superscript differ significantly (P < .05).
[1]No. chicks hatched /no. eggs set (%)
[2]Mean ± SEM.

EXAMPLE 3

Effect of In Ovo Administration of ILK On In Vitro Bactericidal Activity of Heterophils On Day 18 of embryogenesis, 340 (Trial 1) and 234 (Trial 2) fertile white Leghorn eggs (the same eggs from Example 2) were incubated and hatched as described in Example 2. At hatch, whole blood was collected from a subset of 20 chicks per group. Blood within each group was pooled together and heterophils were then isolated from the pooled samples for use in the bactericidal assay described below. Bactericidal activity was collected over two identical trials.

The bactericidal activity of peripheral blood heterophils was evaluated by the method of Stevens and Olsen (*J. Immunol. Methods* 157:225–231 (1993)) in 96-well microtiter plates. Briefly, $1\times10^6$ cfu of nonopsonized SE (in 50µL HBSS) was added to quadruplicate wells containing $2\times10^5$ heterophils (100 µL of $2\times10^6$ per milliliter of HBSS). Control wells contained HBSS alone. In addition, a suspension of $2\times10^7$ cfu SE (100%) in HBSS (100 µL) was diluted to $1.4\times10^7$ cfu SE (70%), $8\times10^6$ cfu SE (40%) and $2\times10^6$ cfu (10%). One hundred microliters of each dilution was added to quadruplicate wells for the construction of a standard curve. The plates were centrifuged (400×g for 5 minutes at 4° C.) to allow maximum bacterial or heterophil contact. The plates were then incubated for 60 minutes at 37° C. After this incubation, heterophils were lysed by adding 50 µL of 0.1% Triton X-100. Fifty microliters of a 0.5 mg/mL solution of 3,3'-[1[(phenylamino) carbonyl]-3,4-tetrazolium]-bis (4-methoxy-6-nitro) benzene sulfonic acid hydrate (XTT) containing 50 µg/mL of 2,3-dimethoxy-5-methyl-1,4-benzoquinone was added to each well and the plates were returned to the incubator for 30 minutes to allow the viable bacteria to reduce the XTT to formazan. The soluble formazan produced by the bacteria was then quantified by measuring the optical densities of each well at 450 nm with an automated ELISA plate reader (Bio-Tel Model EL 311, Winooski, Vt.). A standard curve of bactericidal activity was constructed from the values of the wells containing the known dilutions of bacterial cell numbers, and the relative concentration of bacteria in each quadruplicate set of test wells was calculated using the standard curve. Each plate was compared with its own standard curve to account for day-to-day and plate-to-plate variations. The standard curve was verified by standard plate counts. *Salmonella enteritidis* killing was quantified by extrapolating the percentage of viable SE from the standard curve by using the optical density recorded from each test well. The results were expressed as percentage SE killing, which was calculated by 100-percentage SE viability.

Table 2 illustrates the effect of in ovo administration of ILK to fertile eggs on the in vitro bactericidal activity of heterophils. In trials 1 and 2, in ovo administration of ILK caused a significant increase (29% and 59%, respectively) in the in vitro bactericidal activity of isolated peripheral blood heterophils when the phagocytes were incubated with nonopsonized SE for 60 minutes. It has been previously postulated that ILK was an immunomodulator that conferred protection to chicks against organ infectivity by activating peripheral blood heterophils and that these activated phagocytes migrated to the site of SE infection in the ceca and killed the bacteria. (McGruder et al., *Poultry Sci.* 72:2265–2271 (1993); Kogut et al., *Inflammation* 18:373–388 (1994)). These present results suggest that in ovo administration of ILK enhances bactericidal activity of peripheral blood heterophils against SE in hatched chicks.

TABLE 2

Effect of in ovo administration of immune lymphokines to fertile eggs on in vitro bactericidal activity of heterophils from hatched chicks.

| Trial | In ovo administration | Percentage SE killing |
|---|---|---|
| 1 | untreated | 50[b] |
|   | NILK | 60[b] |
|   | ILK | 85[a] |
| 2 | untreated | 35[b] |
|   | NILK | 37[b] |
|   | ILK | 90[a] |

Data is expressed as percentage SE killing (100 - percentage SE viability). Different letters (a or b) within trials denote significant (P < .05) differences within groups.

EXAMPLE 4

Effect of In Ovo Administration of ILK on *Salmonella enteritidis* Organ Invasion On Day 18 of embryogenesis, 74 (Trial 1) and 340 (Trial 2) fertile White Leghorn eggs were incubated and hatched as described in Example 2. At hatch, chicks were orally challenged with $5 \times 10^4$ cfu SE (0.5 mL of $1 \times 10^5$ cfu/mL). Twenty four hours after SE challenge, chicks were euthanized and their organs (liver and spleen) were cultured for SE. *Salmonella enteritidis* organ invasion data was collected over two trials.

For determination of SE organ invasion, the liver and spleen samples were collected aseptically, macerated and cultured as a combined sample. Organ samples were incubated for 18 hours at 37° C. in tetrathionate broth. After incubation, the broth was streaked on BGA plates containing NO/NA, incubated for an additional 24 hours at 37° C., and examined for the presence of lactose-negative, NO/NA-resistant colonies. Data was reported as percentage SE infected per treatment group.

Table 3 shows the effect of in ovo administration of ILK to fertile eggs on SE organ invasion. In trial 1, ILK administration caused a significant reduction in SE organ invasion (71%) as compared with the NILK treatment group. Similarly, a marked and significant reduction in SE organ invasion was observed in the ILK-treated group as compared with either untreated (63%) or NILK treated chicks (68%) in Trial 2. Because chicks are highly susceptible to salmonellosis during the first 7 days after hatch, it is advantageous to protect chicks immediately after hatch. These results indicate that chicks can acquire substantial protection at hatch by the in ovo administration of ILK.

TABLE 3

Effect of in ovo administration of immune lymphokines to fertile eggs on *Salmonella enteritidis* (SE) organ invasion in hatched chicks.

| Trial | In ovo administration | Percentage SE infected |
|---|---|---|
| 1 | untreated | 80% |
|   | NILK | N.D. |
|   | ILK | 25% |
| 2 | untreated | 75% |
|   | NILK | 55% |
|   | ILK | 25% |

Data is expressed as percentage SE infected. Different letters (a or b) within trials denote significant (P < .05) differences between groups. N.D. = not done. Trial 1: n = 20 (NILK); 18 (ILK). Trial 2: n = 88 (control); 89 (NILK); 94 (ILK).

The foregoing examples are illustrative of the present invention, and are not to be construed as limiting thereof. The invention is defined by the following claims, with equivalents of the claims to be included therein.

That which is claimed is:

1. A method of treating infection in a bird by a pathogenic microbe, comprising administering to said bird in ovo an immune lymphokine preparation in an effective microbe-combating amount, wherein said immune lymphokine preparation has been obtained from a donor animal immunized with an immunogen in an amount effective to stimulate, activate or induce T-cells of said donor animal.

2. A method according to claim 1, wherein said immune lymphokine preparation comprises avian immune lymphokine.

3. A method according to claim 1, wherein said bird is selected from the group consisting of chickens, turkeys, ducks, geese, quail, and pheasant.

4. A method according to claim 1, wherein said bird is selected from the group consisting of chickens and turkeys.

5. A method according to claim 1, wherein said immune lymphokine preparation is administered to said bird in ovo during about the last quarter of in ovo incubation.

6. A method according to claim 1, wherein said bird is a chicken and said immune lymphokine preparation is administered to said bird in ovo on about the fifteenth to about the nineteenth day of incubation.

7. A method according to claim 1, wherein said bird is a turkey and said immune lymphokine preparation is administered to said bird in ovo on about the twenty-first to about the twenty-sixth day of incubation.

8. A method according to claim 1, wherein said immune lymphokine preparation is administered to said bird by injecting the immune lymphokine preparation into the egg in which the bird is contained.

9. A method according to claim 1, wherein said administering step is carried out by administering said immune lymphokine preparation into the region defined by the amnion, the yolk sac, or the air cell.

10. A method according to claim 1, wherein said immunogen is from a microorganism.

11. A method according to claim 10 wherein said microorganism is selected from the group consisting of viruses, bacteria, and protozoa.

12. A method according to claim 11, wherein said microorganism is a bacterium.

13. A method according to claim 12, wherein said bacterium is a *Salmonella* species.

14. A method according to claim 13, wherein said Salmonella species is *Salmonella enteritidis*.

15. A method according to claim 1, wherein said microorganism is a protozoan.

16. A method according to claim 13, wherein said protozoan is an Eimeria species.

17. A method according to claim 16, wherein said Eimeria species is *Eimeria tenella*.

18. A method according to claim 1, wherein said donor animal is a bird.

19. A method according to claim 18, wherein said donor animal is selected from the group consisting of chickens, turkeys, and ducks.

* * * * *